US010327974B2

(12) United States Patent
Levesque et al.

(10) Patent No.: US 10,327,974 B2
(45) Date of Patent: Jun. 25, 2019

(54) HAPTIC IMPLANTS

(71) Applicant: Immersion Corporation, San Jose, CA (US)

(72) Inventors: Vincent Levesque, Montreal (CA);
David M. Birnbaum, Oakland, CA (US); Benoit Paul Belley, San Jose, CA (US); Jamal Saboune, Montreal (CA); Abdelwahab Hamam, Montreal (CA); Ravikumar Patel, Montreal (CA); Christopher Ullrich, Ventura, CA (US); Mohammadreza Motamedi, Montreal (CA); Juan Manuel Cruz-Hernandez, Montreal (CA)

(73) Assignee: IMMERSION CORPORATION, San Jose, CA (US)

( * ) Notice: Subject to any disclaimer, the term of this patent is extended or adjusted under 35 U.S.C. 154(b) by 0 days.

(21) Appl. No.: 15/666,691

(22) Filed: Aug. 2, 2017

(65) Prior Publication Data
US 2019/0038496 A1 Feb. 7, 2019

(51) Int. Cl.
A61H 1/00 (2006.01)
G08B 6/00 (2006.01)
A61F 2/02 (2006.01)
A61B 90/98 (2016.01)
A61H 23/02 (2006.01)

(52) U.S. Cl.
CPC ............ *A61H 1/00* (2013.01); *A61B 90/98* (2016.02); *A61F 2/02* (2013.01); *A61H 23/0245* (2013.01); *A61H 23/0263* (2013.01); *G08B 6/00* (2013.01); *A61H 2201/10* (2013.01); *A61H 2201/123* (2013.01); *A61H 2201/1215* (2013.01); *A61H 2205/067* (2013.01)

(58) Field of Classification Search
CPC .. A61H 1/00; A61H 23/0245; A61H 2201/10; A61H 2201/123; A61H 2201/1215; A61H 23/0263; A61H 2205/067; A61B 90/98; A61F 2/02; G08B 6/00
USPC ................ 340/572.1–572.8, 573.1, 4.1, 4.12
See application file for complete search history.

(56) References Cited

U.S. PATENT DOCUMENTS

| 6,198,395 B1* | 3/2001 | Sussman ................ A61F 9/08 340/407.1 |
| 8,362,882 B2 | 1/2013 | Heubel et al. |
| 8,665,241 B2 | 3/2014 | Heubel et al. |
| 9,058,728 B2 | 6/2015 | Fantauzza |
| 2005/0134452 A1* | 6/2005 | Smith ................ A01K 11/008 340/539.12 |
| 2012/0062371 A1 | 3/2012 | Radivojevic et al. |
| 2015/0005606 A1* | 1/2015 | Honore ............. A61B 5/14532 600/365 |

(Continued)

OTHER PUBLICATIONS

Bellan and Bossis, "Field Dependence of Viscoelastic Properties of MR Elastomers," Int. J. Mod. Phys. B. 16:2447-2453 (2002).

(Continued)

*Primary Examiner* — Brian Wilson
(74) *Attorney, Agent, or Firm* — Medler Ferro Woodhouse & Mills PLLC

(57) ABSTRACT

This disclosure relates to haptic devices for implantation in a human subject. Such haptic devices can include various actuators, including both active and passive haptic actuators, for providing feedback to a user.

12 Claims, 7 Drawing Sheets

(56) References Cited

U.S. PATENT DOCUMENTS

| | | | |
|---|---|---|---|
| 2015/0087249 A1* | 3/2015 | Pugh | H04B 1/385 455/90.3 |
| 2016/0103489 A1* | 4/2016 | Cruz-Hernandez | G06F 1/163 345/161 |
| 2017/0031159 A1* | 2/2017 | Pugh | A61B 5/4809 |

OTHER PUBLICATIONS

Palleau, et al., "Reversible patterning and actuation of hydrogels by electrically assisted ionoprinting," Nature Communications 4:2257 (2013).

Behl and Lendlein, "Shape Memory Polymers," MaterialsToday, vol. 10, pp. 20-28 (2007).

"Tiny Tools Offer New Biopsy Approach," Jul. 9, 2013, available at: https://engineering.jhu.edu/news/2013/07/09/tiny-tools-offer-new-biopsy-approach/#.WfnvdeYm7MG.

D. Berg., "I Have a Magnet Implant in My Finger," Mar. 22, 2012, available at: https://gizmodo.com/5895555/i-have-a-magnet-implant-in-my-finger.

\* cited by examiner

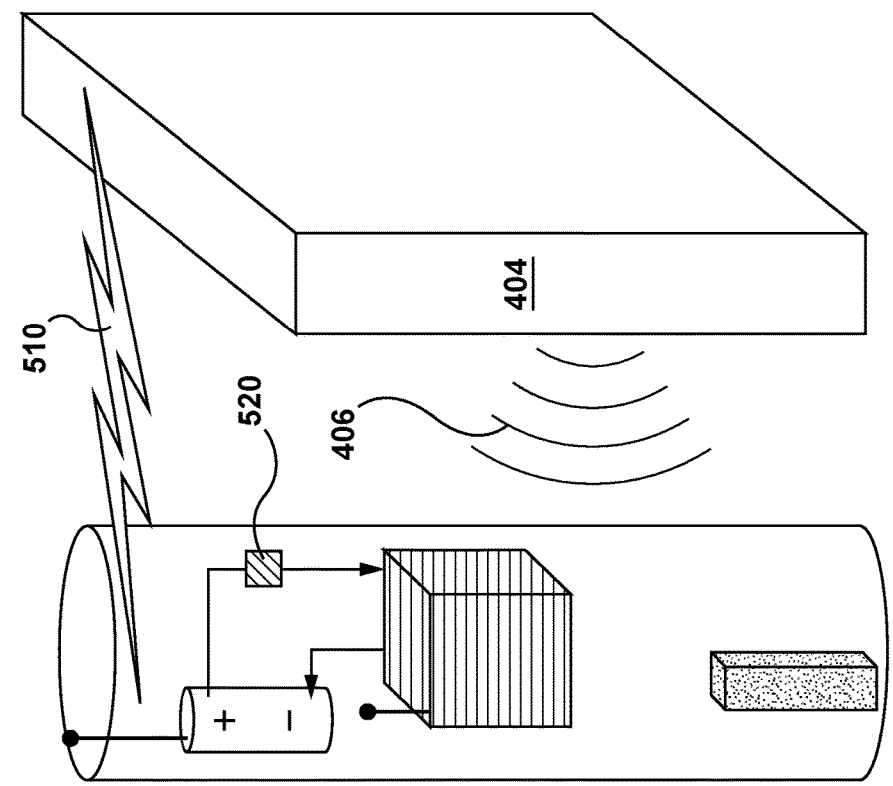
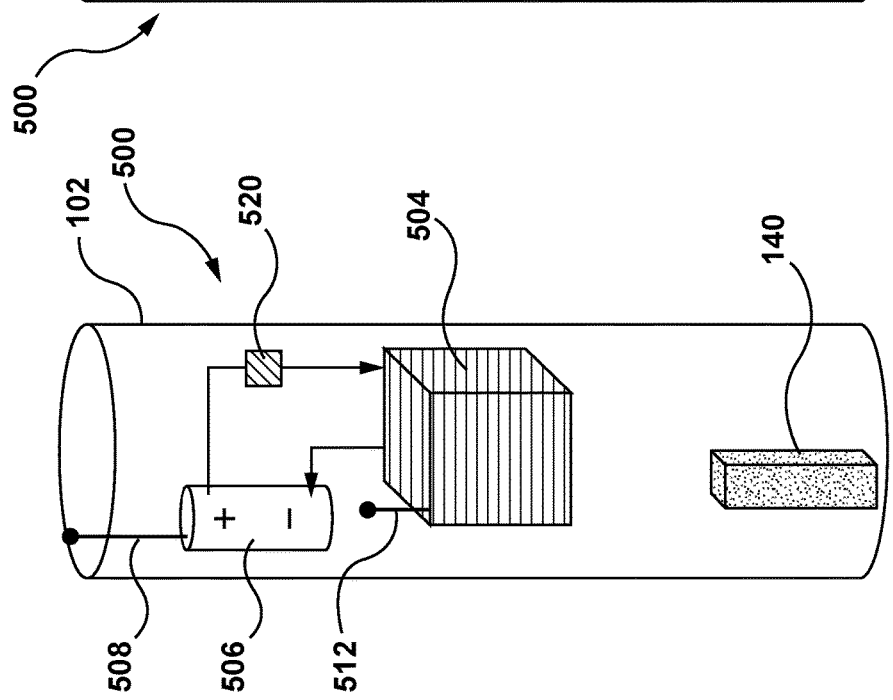
FIG. 5B
FIG. 5A

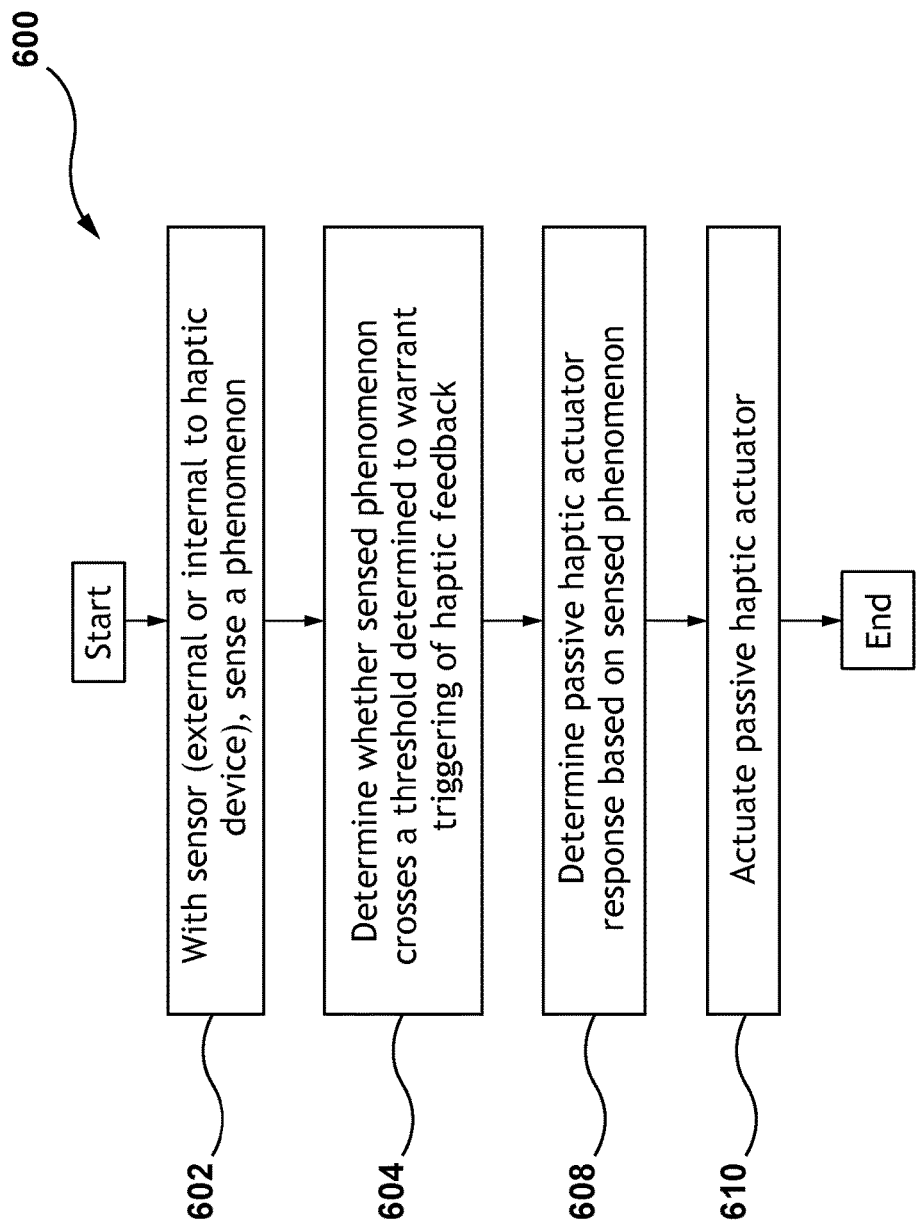

HAPTIC IMPLANTS

TECHNICAL FIELD

This disclosure relates to haptic devices for implantation in a human subject. Such haptic devices can include various actuators, including both active and passive haptic actuators, for providing feedback to a user.

BACKGROUND

Producing haptic feedback typically includes either direct interaction between an object and a user. Alternatively, the body of a user can be augmented with a haptic actuator. The first solution is practical for many devices, but does not scale to all objects in a user's environment particularly as objects in a user's environment gain interactive qualities ("the internet of things" concept). The second solution scales to an arbitrary number of objects but typically requires the user to wear a device with a haptic actuator, which can be cumbersome or inconvenient.

What is needed is a mechanism for providing haptic feedback that does not rely on haptic actuation inside an external device or the wearing of a device.

SUMMARY

In order to address these needs, provided herein are implantable haptic devices.

In embodiments, provided herein is a passive haptic device, including a biocompatible encapsulating material, and a passive haptic actuator contained within the encapsulating material. In embodiments, the passive haptic device is configured for implanting within a body of a user. In further embodiments, the haptic actuator, in response to an actuation signal from an actuation component, provides haptic feedback to the user, and in still further embodiments, the passive haptic device does not comprise a power source. Instead, the passive haptic device receives power from a power source external to the body of the user.

Also provided herein is an active haptic device, including a biocompatible encapsulating material, an active haptic actuator contained within the encapsulating material, and a power source for powering the active haptic actuator that is electrically coupled to the active haptic actuator, and is configured for implanting within the body of a user. In embodiments, the active haptic device is configured for implanting within a body of a user, and the active haptic actuator, in response to an actuation signal from an actuation component, provides haptic feedback to the user.

In additional embodiments, provided are methods of providing haptic feedback to a user. The methods suitably include sensing a phenomenon, determining whether the phenomenon crosses a threshold sufficient to trigger a haptic feedback, determining an active haptic actuator response or a passive haptic actuator response based on the phenomenon, and actuating the active haptic actuator response or the passive haptic actuator response.

BRIEF DESCRIPTION OF THE DRAWINGS

The foregoing and other features and aspects of the present technology can be better understood from the following description of embodiments and as illustrated in the accompanying drawings. The accompanying drawings, which are incorporated herein and form a part of the specification, further serve to illustrate the principles of the present technology. The components in the drawings are not necessarily to scale.

FIGS. 5A-5B show an active haptic device in accordance with an embodiment hereof.

FIGS. 6A-6B show flowcharts of providing haptic feedback via haptic devices in accordance with embodiments hereof.

DETAILED DESCRIPTION

Various embodiments will be described in detail, some with reference to the drawings. Reference to various embodiments does not limit the scope of the claims attached hereto. Additionally, any embodiments set forth in this specification are not intended to be limiting and merely set forth some of the many possible embodiments for the appended claims.

Whenever appropriate, terms used in the singular also will include the plural and vice versa. The use of "a" herein means "one or more" unless stated otherwise or where the use of "one or more" is clearly inappropriate. The use of "or" means "and/or" unless stated otherwise. The use of "comprise," "comprises," "comprising," "include," "includes," "including," "has," and "having" are interchangeable and not intended to be limiting. The term "such as" also is not intended to be limiting. For example, the term "including" shall mean "including, but not limited to."

In exemplary embodiments, provided herein are passive haptic devices. As used herein, a "passive haptic device" refers to a device for providing haptic feedback to a user, wherein the haptic device does not include a power source. Instead, a passive haptic actuator within a passive haptic device functions by interacting with an external actuation component (outside of the body of the user) and reacts to an external actuation by modifying the conformation, position, shape, location or orientation of the haptic actuator.

As used herein "haptic feedback" or "haptic feedback signal" refer to information such as vibration, texture, and/or heat, etc., that are transferred, via the sense of touch, from a haptic device as described herein, to a user.

Figure 1B:
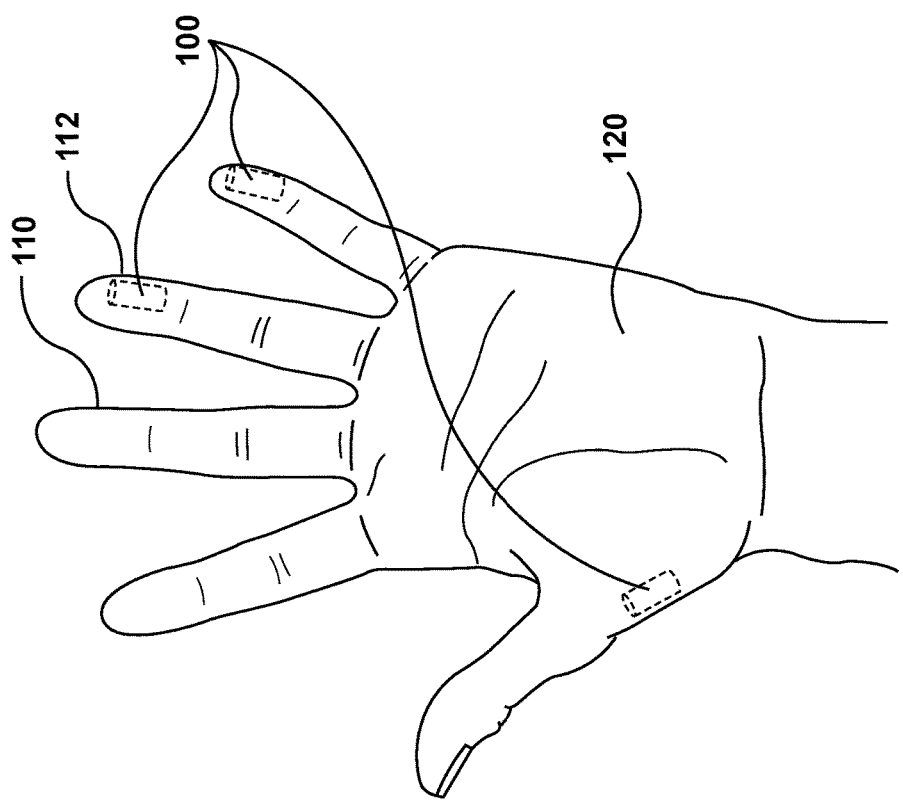
FIG. 1B shows some possible locations for an implanted passive haptic device in accordance with an embodiment hereof.
Figure 1A:
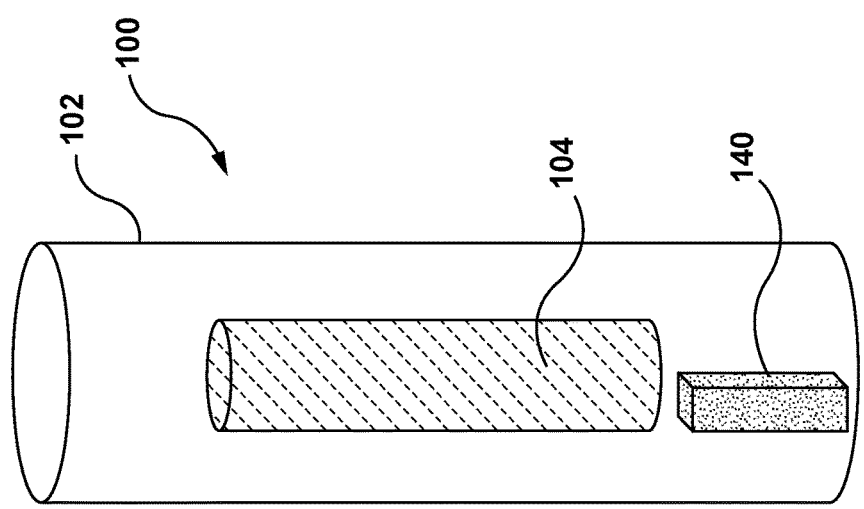
FIG. 1A shows a passive haptic device in accordance with an embodiment hereof.

An exemplary passive haptic device 100, shown in FIG. 1A, includes, for example, a biocompatible encapsulating material 102 and a passive haptic actuator 104 contained within the encapsulating material. As described in detail herein, passive haptic device 100 is configured for implanting or implantation within a body of a user. That is, passive haptic device 100 can be readily implanted or inserted into a body of a user by implantation, insertion or embedding under the skin of a user, including into muscle tissue, bone tissue, subdermal tissue, cartilage, various organs, etc. Implantation or insertion of passive haptic device 100 can occur via the use of a needle, catheter, etc., or can be carried out via a surgical procedure.

For example, as shown in FIG. 1B, passive haptic device 100 can be implanted under the skin of a hand of a user, including in a finger 110, a fingertip 112, or a palm 120. Passive haptic device 100 an be implanted in any area or body part of a user, for example, the hands, feet, head, face, ears, legs, arms, trunk, chest, back, etc. In embodiments, passive haptic actuator 104 within passive haptic device 100, in response to an actuation signal 406 from an external actuation component 404 (see FIG. 4), provides haptic feedback to a user 402.

The shape and size of passive haptic device 100 shown in FIG. 1A is for illustrative purposes only, and it should be understood that any suitable shape can be used, for example, spherical, rectangular, square, oblong, cylindrical, capsule-shaped, egg-shaped, asymmetrically shaped, thread-like shaped, etc. In addition, it should be understood that the size and shape of passive haptic actuator 104 shown in FIG. 1A is for illustrative purposes only, and any shapes such as spherical, rectangular, square, oblong, cylindrical, capsule-shaped, egg-shaped, non-uniform shaped, asymmetrically shaped, thread-like shaped, etc., can be used. Furthermore, a plurality of passive haptic actuators 104 can be included in passive haptic device 100, and encapsulated within biocompatible encapsulating material 102, for example a plurality of 2, 3, 4, 5, 6, 7, 8, 9, 10, 20, 50, 100, 200, 500, etc.

The macro-scale shape of passive haptic actuator 104 (as well as its surface features as described herein) can be used to provide haptic feedback to a user, such that when the passive haptic actuator moves, translates, rotates, vibrates, etc., a user feels the passive haptic actuator 104 under a surface of his or her skin, or against a muscle, bone, nerve, cartilage, etc., of his or her body. For example the use of a spherical or ball-shaped passive haptic actuator 104 would allow for easy and rapid repositioning within a body of a user by rolling or translating the ball. For example by using an electromagnet, passive haptic actuator 104 can be moved to a desired portion of a user's body where haptic feedback is desired, including different portions of finger 110 or finger tips 112 of the user.

As described herein, in exemplary embodiments, passive haptic actuator 104 comprises a magnetic material. Exemplary magnetic materials which can be used, include iron, nickel, cobalt, alloys of rare earth metals, and naturally occurring minerals such as lodestone. In further embodiments, the magnetic material can comprise magnetic particles, including micro-particles or nanoparticles of the magnetic material. For example, the magnetic material can comprise a matrix of a polymeric material with magnetic particles embedded therein. The polymeric material can be chosen from those described herein, including for example, soft polymeric materials, such as silicone, natural rubber and synthetic rubber, or a rigid material, such as polyethylene terephthalate (PET), polycarbonate (PC), polyethylene naphthalene (PEN), silicon based polymers, polyurethanes, thermoplastics, thermoplastic-elastomers, thermoset polymers, and polymer composites filled with natural or synthetic fillers. The magnetic particles can be nanoparticles of magnetic materials such as carbon iron nanoparticles or rare-earth (e.g., neodymium) nanoparticles.

Figure 2C:
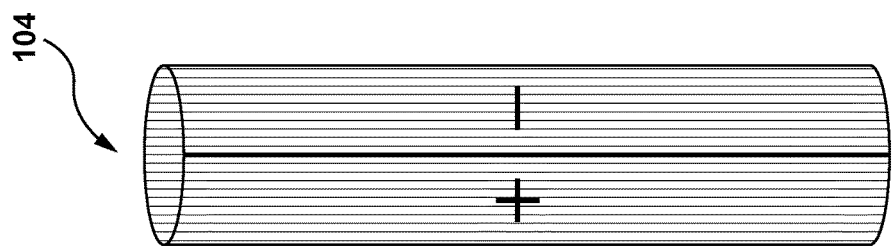
FIGS. 2A-2C show passive haptic actuators in accordance with embodiments hereof.
Figure 2B:
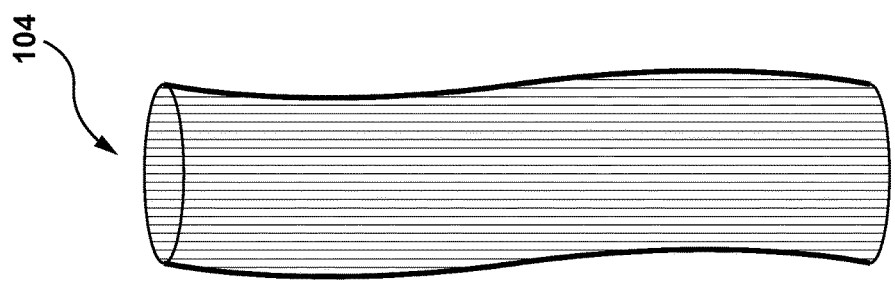
Figure 2A:
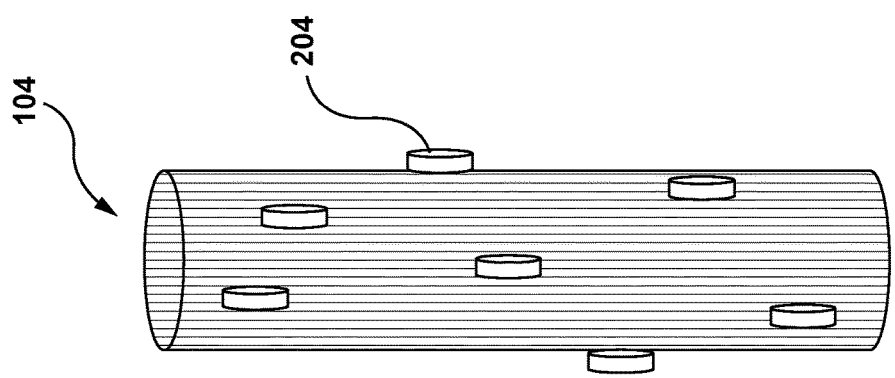

As shown in FIGS. 2A-2C, in embodiments, passive haptic actuator 104 can have a programmed surface. As used herein, "programmed surface" refers to surface characteristics or structural features that are included, implemented, or otherwise formed on passive haptic actuator 104, prior to inclusion in the passive haptic devices described herein (i.e., prior to encapsulation and implantation). For example, as shown in FIG. 2A, passive haptic actuator 104 can include surface features 204 that impart a rough or textured surface, or a change in the frictional coefficient of a surface. For example raised regions, indented regions, additional structures, cracks, cut-outs, protrusions, bumps, holes, etc., can all be used to create surface features 204 on an outer surface of passive haptic actuator 104. In further embodiments, as shown in FIG. 2B, a programmed surface can be implemented by providing the passive haptic actuator with a wavy or bent structure. In embodiments that employ passive haptic actuator 104 having a programmed surface, movement, rotation, a change in position or orientation of the passive haptic actuator (as the result of an actuation by an external actuation component 404), results in the passive haptic actuator being felt or perceived by a user, and thus, a haptic feedback being provided to the user (for example, in a fingertip of a user where the passive haptic device is located).

In further embodiments, as shown in FIG. 2C, passive haptic actuator 104 can include a programmed polarity. That is, in embodiments where a magnetic material is utilized to prepare passive haptic actuator 104, the "programmed polarity" of the passive haptic actuator can be included, implemented, or otherwise imparted to passive haptic actuator 104, prior to inclusion in the haptic devices described herein (i.e., prior to encapsulation and implantation), by specifically orienting the magnetic or electric polarity of the passive haptic actuator in a desired orientation. For example, in embodiments, a programmed polarity can be implemented in the passive haptic actuator, such that, for example, in response to an external electromagnetic field, the passive haptic actuator rotates, spins, moves, travels, or orients in a particular manner, such that it is felt by a user and provides a haptic feedback to the user. The programmed polarity can also provide a response to an actuation signal by spinning at a particular rate (e.g., 1-100 rotations/second, or higher, for example 1000 rotations/second, or even higher at 10-100 Hz to kHz frequencies), or can simply provide an attractive force or a repulsive force relative to an external device, to thereby provide a haptic feedback to a user that indicates the external device has interacted with the passive haptic device. For example, an external electromagnet can be used to vary magnetic polarity, thereby generating attractive/repulsive forces. The electromagnet can be controlled using an amplifier that sends to the electromagnet an alternative signal (voltage/current) where the polarity of the signal is proportional to the polarity of the magnetic field.

Similarly, using electrets, the surface of passive haptic actuator 104 can be polarized in a certain way such that when an external electrostatic field is present, a repulsive/attractive force can be generated.

In additional embodiments, the programmed surface of passive haptic actuator 104 can change conformation in response to an actuation signal. For example, in response to an electromagnetic field, the programmed surface can transform or modify a surface characteristic to generate a haptic feedback. In embodiments, the change in conformation can occur, for example, by an extension or a protrusion of a section of the passive haptic actuator, or a warping or a bending of the shape, resulting in contact with a user, and thereby providing haptic feedback. By utilizing appropriately sized passive haptic actuators 104 (e.g., those large enough to be felt through biocompatible encapsulating material 102 when they move), or actuators that sufficiently contact biocompatible encapsulating material 102 (e.g., sufficient movement within the biocompatible encapsulating material so as to translate haptic feedback beyond the biocompatible encapsulating material).

Figure 3B:
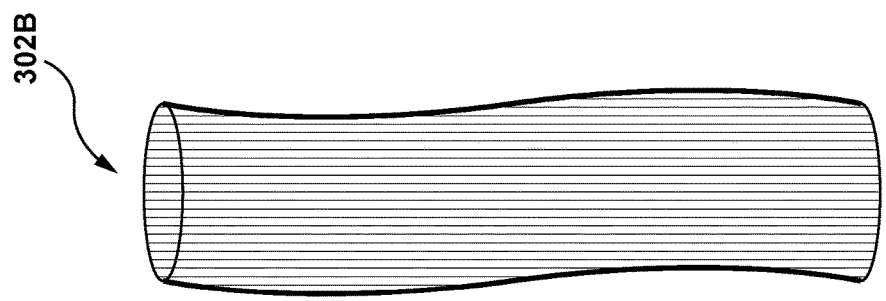
FIGS. 3A-3B show further passive haptic actuators in accordance with embodiments hereof.
Figure 3A:
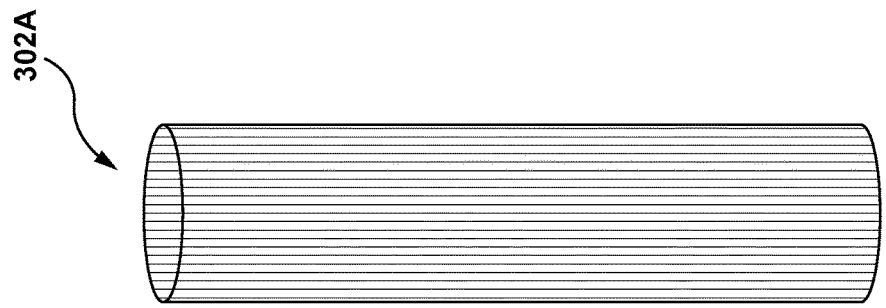

In embodiments, passive haptic actuator 104 can comprise a smart material. Examples of smart materials include various polymers, including electroactive polymers, shape memory alloys, shape memory polymers (SMP), and macro fiber composites (MFC). With reference to FIGS. 3A and 3B, a smart material haptic actuator 302A can be included in passive haptic devices described herein in a conformation shown in FIG. 3A. In response to an actuation signal (see FIG. 4), the smart material that comprises the haptic actuator deforms to deformed smart material haptic actuator 302B having, for example, a wavy, textured, extended, compressed, warped, bent, or otherwise modified shape. It is the deformation of smart material haptic actuator 302A to deformed smart material haptic actuator 302B that results in a haptic feedback being felt by a user.

In embodiments, as described herein, actuation signal 406 can comprise an electromagnetic field or a thermal energy. In other embodiments, actuation signal 406 can include an electric field, infrared radiation, ultraviolet or visible light, ultrasound, etc. In embodiments where an actuation signal comprises an electromagnetic field, suitably passive haptic actuator 104 comprises a magnetic material such that the passive haptic actuator interacts and changes, moves, or otherwise responds to the actuation signal to provide a haptic feedback, as described herein. In embodiments where a thermal energy is used, external actuation component 404 suitably includes some type of a thermal energy source, including laser, radio frequency, ultrasound, light, conductive or inductive heating elements, etc., to provide thermal energy. In such embodiments, passive haptic actuator 104 can respond to the thermal energy, for example, by changing conformation or shape, deforming, etc., to provide a haptic feedback to a user.

In exemplary embodiments, external actuation component 404 may comprise an electromagnet that can be driven to output a constant or varying magnetic field. Such an actuation component may induce an attractive and/or repulsive force on passive haptic actuator 104. Other exemplary external actuation components 404 include an air coil (or air core coil), an induction coil, a thermal energy source such as a resistor, an electrostatic generator, an ultrasound generator, an ultraviolet light source, or a visible light source, including a laser light source, etc.

In further embodiments, passive haptic actuator 104 can include a material such as gallium, a metal that is a liquid at body temperature, but a solid at room temperature. In response to an external cooling (e.g., via a thermal sink or other cooling device), a temperature of passive haptic actuator 104 may be reduced, causing it to solidify, and thereby providing a haptic feedback to a user who notices or feels a change in the state of the material (e.g, liquid to solid) within the passive haptic device, or can be perceived as a change in temperature.

As shown in FIG. 1A, in further embodiments, passive haptic device 100 can further comprise a radio-frequency identification (RFID) tag 140, contained within biocompatible encapsulating material 102. RFID tags are well known in the art and typically contain electrically stored information, and can be powered from a RFID reader external to a user, which emits interrogating radio waves. Stated another way, generally, a RFID reader transmits an encoded radio signal to interrogate the tag, wherein the RFID tag receives the signal and then responds with its identification and other information, which may be stored in a non-volatile memory thereof. In embodiments, in response to the interrogating radio waves, the RFID tag provides information, such as, the location, orientation, status, etc., of the RFID tag. RFID tags suitably contain at least two parts: an integrated circuit for storing and processing information, modulating and demodulating a radio-frequency (RF) signal, collecting DC power from an incident reader signal, and performing other specialized functions; and an antenna for receiving and transmitting a signal. The RFID tag may further include either fixed or programmable logic for processing the transmission and sensor data (use of the implants as sensors described herein), respectively. The RFID tag can also contain information about the haptic device(s) that are encapsulated in the biocompatible encapsulating material. For example, the RFID can identify the type(s) of haptic actuator(s) within the biocompatible encapsulating material (piezoelectric, smart material, etc.), and/or the type of actuation signal that may be required (e.g., magnetic field, thermal, etc.), as well as the frequency or wave form needed for actuation (e.g., pulse, square wave, sine wave, etc.). The RFID tag can also be utilized for non-haptic feedback functionality, including payment or credit card information, health information, personal identification information, etc.

Examples of suitable biocompatible encapsulating materials 102 include various glasses, metals, polymers, etc., including, but not limited to, various silicones, poly(ethylenes), poly (propylenes), poly(tetrafluorethylenes), poly (methacrylates), etc. Exemplary metals include titanium, iron, cobalt, chromium, tantalum, etc. Such materials can be readily shaped or processed in the form of a sphere, a capsule or other structure useful for containing the haptic actuators described herein. In embodiments, passive haptic device 100 is in the form of a prosthetic body part. For example, passive haptic device 100 can be prepared and shaped so as to take the form of a fake tooth, a fake nail, a bone replacement or a bone implant, etc.

In further embodiments, provided herein are active haptic devices. As used herein, an "active haptic device" refers to a device for providing a haptic feedback to a user, wherein the haptic device includes a power source which is electrically coupled to a haptic actuator, and is configured for implanting within the body of a user, and thus provides power to the haptic actuator from within the user. Active haptic devices, as described herein, may include replaceable or rechargeable power supplies.

Figure 4:
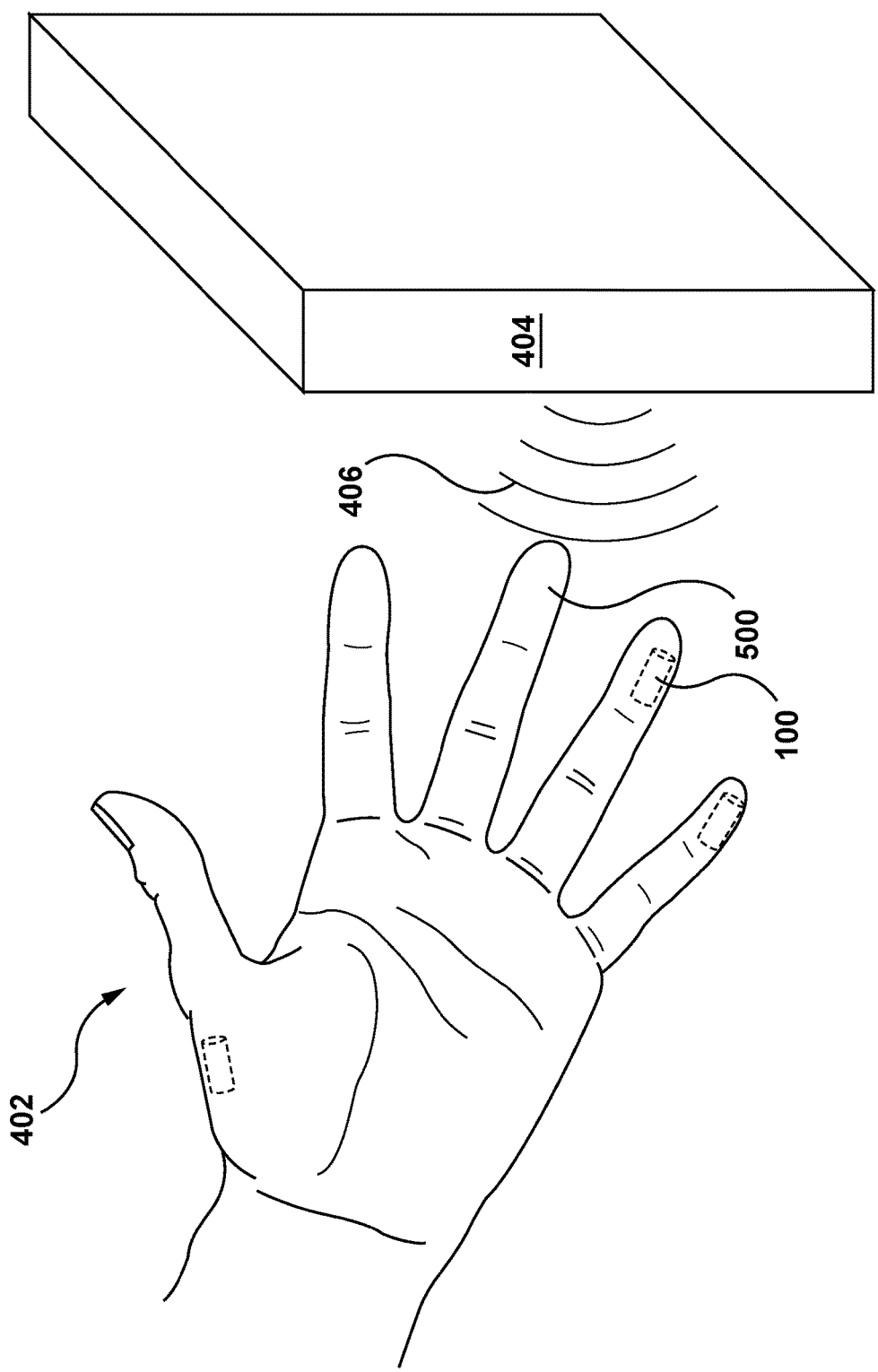
FIG. 4 shows the actuation of a passive haptic device in accordance with an embodiment hereof.

In embodiments, for example as shown in FIG. 5A, an active haptic device 500 includes biocompatible encapsulating material 102 and an active haptic actuator 504 contained within the encapsulating material. Active haptic device 500 further includes a power source 506 that is electrically coupled thereto and that is configured for powering the active haptic actuator 504. As used herein, "electrically coupled" includes wired connections and wireless connections for providing power. As shown in FIG. 4, active haptic device 500 is configured for implanting within a body of a user, as described herein, for example in a finger or a hand of a user, or other body parts or areas of a user. While power source 506 is suitably contained within biocompatible material 102, and thus configured for implantation, in other embodiments, power source 506 can be provided in a separate biocompatible structure or capsule, or otherwise configured to be implanted, within the body of a user.

As illustrated in FIG. 5B, in response to an actuation signal 406 from external actuation component 404, active haptic device 500 provides a haptic feedback to a user for example by modifying its shape, etc. As shown in FIGS. 5A and 5B, in embodiments, power source 506 can include an antenna 508 for receiving a recharging signal 510 for recharging power source 506 (i.e., when power source 506 is a rechargeable power source). This recharging can occur through an inductive power source by interaction across the skin with an external charger. Inductive power sources can include an induction coil to create an alternating electromagnetic field from within a charging base, and a second induction coil in the active haptic device to take power from the electromagnetic field and convert it back into electric current to charge the inductive power source, e.g., battery. In additional embodiments, power source 506 can be a dynamic or self-charged power source, including mechanisms that use a body's motion (piezoelectric) or heat (thermal power generation) or ionic characteristics (salt concentration, or pH), to provide a self-powered system. Power source 506 can also be a replaceable battery, for example.

Exemplary active haptic actuators 504 may include, for example, an eccentric rotating mass (ERM) actuator, a linear resonant actuator (LRA), a materials-based heavy duty actuator, a piezoelectric actuator, a voice coil actuator, an electro-active polymer (EAP) actuator, a shape memory alloy, a pager, a DC motor, an AC motor, a moving magnet actuator, a smartgel, an electrostatic actuator, an electrotactile actuator, a deformable surface, an electrostatic force (ESF) device, an ultrasonic friction (USF) device, or any other haptic output device or collection of components that perform the functions of a haptic actuator or that are capable of outputting haptic feedback. Multiple haptic output devices, or different-sized haptic output devices, may be used to provide a range of vibrational frequencies, and may be actuated individually or simultaneously. Various examples may include multiple haptic output devices that have the same type, or a combination of different types, of haptic output devices.

Additional haptic actuators include, for example, actuators based on an "electroactive material," which refers to a material that exhibits a change in shape or size when stimulated by an electric field (either direct or alternating current). Exemplary electroactive materials, as described herein, include electroactive polymers and piezoelectric materials. Exemplary electroactive polymers include polymers such as, but not limited to, poly(vinylidene fluoride), poly(pyrrole), poly(thiophene), poly(analine) and mixtures, co-polymers, and derivatives thereof. Exemplary classes of electroactive polymers include dielectric and ionic polymers. Dielectric polymers change shape in response to an electrostatic force between two electrodes which squeeze the polymer. Dielectric polymers are capable of very high strains and are fundamentally a capacitor that changes its capacitance when a voltage is applied by allowing the polymer to compress in thickness and expand in area due to the electric field. Ionic polymers undergo a change in shape or size caused by the displacement of ions inside the polymer. Generally, only a small amount of electric potential is required (on the order of a few volts) for actuation, but a higher electrical power is often needed for actuation, and energy may be needed to keep the actuator at a given position. In addition, some polymers require the presence of an aqueous environment to maintain the ionic flow. Exemplary piezoelectric materials include, but are not limited to, barium titanate, hydroxyapatite, apatite, lithium sulfate monohydrate, sodium potassium niobate, quartz, lead zirconium titanate (PZT), tartaric acid and polyvinylidene difluoride fibers. Other piezoelectric materials known in the art can also be used in the embodiments described herein.

The biocompatible encapsulating material can include multiple different haptic actuators, i.e., 2, 3, 4, 5, 6, 7, 8, 9, 10, 15, 20, 25, 30, 40, 50, etc., haptic actuators, as described herein. The haptic actuators can be active or passive, and can be of different nature, i.e., combinations of smart materials, piezoelectrics and mechanical actuators. The combinations of actuators can be utilized together or separately to provide haptic feedback.

Active haptic actuator 504 can provide various forms of haptic feedback, including for example, vibration, deformation, electro-stimulation, electrostatic friction or feedback, heating, etc.

In embodiments, as described herein, active haptic actuator 504 can further include a wireless communication device 512, for example, an antenna. Wireless communication device 512 is used to receive actuation signal 406 from external actuation component 404, thereby providing haptic feedback to the user by actuating active haptic actuator 504. Suitably, a switch 520 can also be included to connect or disconnect the power to haptic actuator 504, or otherwise control when the haptic actuator 504 is made active.

Active haptic device 500 can also further comprise RFID tag 140, as described herein. In embodiments, as detailed herein, active haptic device 500 can be in the form of a prosthetic body part. Additional electronics necessary for driving the active haptic device and charging the power source are also to be included in biocompatible encapsulating material 102. In general, such additional electronics will be encapsulated within the device, though can also be placed along the outside, or as part of or integrated into the surface, of, biocompatible encapsulating material 102.

The amount of power provided by power source 506 is suitably on the order of about 0.1 Watts (W) to about 10 W, or more suitably about 0.5 W to about 5 W, or about 1 W to about 5 W, or about 0.5 W, about 1 W, about 2 W, about 3 W, about 4 W or about 5 W. Exemplary power sources 506 include inductive power sources, as well as various battery packs and solar energy sources. Power source 506 can also include a re-chargeable system, for example, a system capable of recharging through the use of a piezoelectric material.

The location, orientation and placement of active and passive haptic devices described herein (referred to herein collectively as "haptic devices") in a user are important factors when considering how and where to implant or insert the haptic devices in a user. In general, the haptic devices described herein are placed under the skin of a user, generally within a few millimeters to a few centimeters below the skin surface, so as to provide a tactile sensation to a user. For example, placing the haptic devices at or near the surface of a user's fingertip is suitable for interactions where a user's finger would be the primary part that would interact with the external device, for example, via a touchpad, number pad, payment terminal, or other finger-touch interface. In other embodiments, the haptic devices can be implanted much deeper into tissue or organs, or can be placed near muscle spindles or a bone to provide haptic feedback or sensation to a larger part of a user's body. The haptic devices can also be placed near a nerve of a user to provide direct stimulation with an electrical current.

For surface or near-surface implementations, the use of an RFID tag in the devices allows for easy identification by an external device and for the haptic devices to interact readily with the external device or interface. Examples of external devices include, for example, touchscreens, touchpads, cellular phones, tablets, gaming consoles, bank machines, payment terminals, point of sale devices, purchasing kiosks or keypads at various stores, etc., automobile consoles, computers, laptops, etc. In additional embodiments, the external devices can be devices that do not require physical or close-physical (almost touching) interaction to initiate external actuation signal 404, for example, a watch, computer, game console, automobile, etc., located at some distance from the user.

In embodiments, the same active or passive haptic device can be used in different environments, or separate active and passive haptic devices, to interact with different environments/devices. For example, the haptic actuators described herein can be implanted in a user's finger, and allow for interaction with various components of an automobile, including warming sensors, etc., on a steering wheel. The same haptic actuators (or separate if desired) can also interact with other devices as described herein, including sales kiosks or automated tellers, as well as gaming or virtual reality systems. The haptic actuators can thus be made to interact in a generic fashion, with various different devices and under different scenarios.

Exemplary feedback or signals that can be provided by an external device, include, for example, indications of incoming messages or communication from a third party, warning signals, gaming interaction, driver awareness signals, computer prompts, etc.

In further embodiments, the haptic devices described herein can be integrated with or be part of a virtual reality or augmented reality system. In such embodiments, the haptic devices can provide haptic feedback to a user as he or she interacts with a virtual or augmented reality system, providing responses or feedback initiated by the virtual reality or augmented reality components and devices.

In embodiments, multiple haptic devices can be implanted or inserted into a user. In certain embodiments, for example, each finger of a user can have a haptic device as described herein (either passive or active, or some of each) inserted. In other embodiments, multiple haptic devices can be implanted or inserted in the same area or body part of a user. For example, multiple haptic devices can be implanted or inserted in the same fingertip, creating a flowing or moving sensation when actuated collectively or sequentially.

Also provided herein are methods of providing haptic feedback to a user, which include receiving a haptic signal and actuating an active haptic actuator response or a passive haptic actuator response. Examples of haptic signals can come from various sources such as external mobile phones, tablets, computers, automobiles, etc., and can signal incoming messages, phone calls, alerts, etc., as described herein. Exemplary active haptic actuator responses include vibration, deformation, electro-stimulation, electrostatic friction or feedback, or heating. Exemplary passive haptic actuator responses include rotation, a change in shape or a movement.

Also provided herein are methods of providing haptic feedback to a user, including receiving a signal, determining an active haptic actuator response or a passive haptic actuator response based on the signal, and actuating the active haptic actuator response or the passive haptic actuator response. Examples of signals can come from various sources such as external mobile phones, tablets, computers, automobiles, etc., and can signal incoming messages, phone calls, alerts, etc., as described herein. In addition, signals can also be generated by the user, and include manual touching or rubbing over a portion of the body which include the implanted sensors and actuators.

Figure 6B:
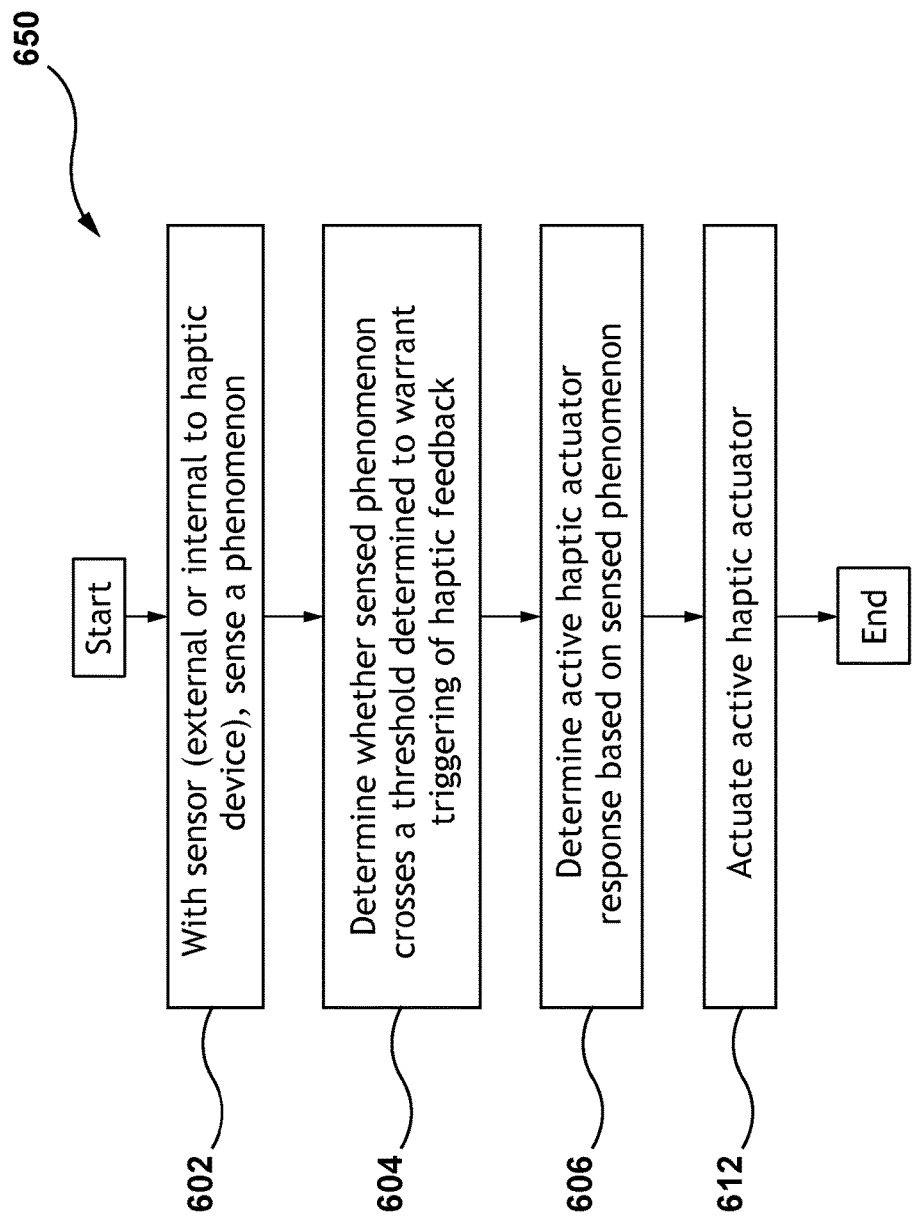

FIGS. 6A-6B show flowchart 600 of a haptic feedback process for active haptic devices and flowchart 650 shows an additional haptic feedback process for passive haptic devices as described herein. For each type of haptic devices, a sensor (including both sensors internal to the haptic devices as well as associated with external devices, including for example, external actuation component 404), is used in block 602 to sense a phenomenon. In embodiments, the sensor is an implanted sensor, such as a component of the haptic device which interacts with an external device. Examples of phenomena, include, for example, touching or close approach of a user, an external signal from an additional device, a voice command, a computer signal, etc. In block 604, it is determined whether a sensed phenomenon crosses a threshold sufficient to trigger a haptic feedback to a user. For example, it is determined that the user's finger touching a touchpad or touch device is sufficient to trigger a haptic feedback. Then, for the active haptic actuators described herein, in block 606, a response is determined based on the sensed phenomenon. For example, it may be determined that the active haptic actuator is to provide a vibrational response to the user. Similarly, for the passive haptic actuators, in block 608, a response is determined based on the sensed phenomenon. For example, it may be determined that the passive haptic actuator is to be rotated. In response to these determinations, in blocks 610 or 612, the active or passive haptic actuators are actuated, thereby providing a haptic feedback to the user.

The various embodiments described above are provided by way of illustration only and should not be construed to limit the claims attached hereto. Those skilled in the art will readily recognize various modifications and changes that may be made without following the example embodiments and applications illustrated and described herein, and without departing from the true spirit and scope of the following claims.

What is claimed is:

1. A passive haptic device, comprising:
   a biocompatible encapsulating material;
   a passive haptic actuator having a programmed polarity contained within the biocompatible encapsulating material; and
   a sensor contained with the biocompatible encapsulating material configured to determine whether a sensed phenomena crosses a threshold sufficient to trigger haptic feedback,
   wherein the passive haptic device is configured for implanting within a body of a user,
   wherein the passive haptic actuator, in response to an actuation signal from an external actuation component or in response to the sensed phenomena crossing the threshold, provides the haptic feedback to the user, and wherein the passive haptic device does not include a power source.

2. The passive haptic device of claim 1, wherein the passive haptic actuator comprises a magnetic material.

3. The passive haptic device of claim 1, wherein the passive haptic actuator comprises a smart material.

4. The passive haptic device of claim 1, further comprising: a radio-frequency identification (RFID) tag contained within the biocompatible encapsulating material.

5. The passive haptic device of claim 1, wherein the actuation signal comprises an electromagnetic field or thermal energy.

6. The passive haptic device of claim 1, wherein the passive haptic device is in the form of a prosthetic body part.

7. A method of providing haptic feedback to a user, comprising:
   a. sensing a phenomenon via a sensor contained within a biocompatible encapsulating material of a haptic device implanted within a body of the user, the haptic device further including a passive haptic actuator having a programmed polarity contained within the biocompatible encapsulating material;

b. determining whether the phenomenon crosses a threshold sufficient to trigger the haptic feedback;

c. determining a passive haptic actuator response based on the phenomenon; and d. actuating the passive haptic actuator response.

8. The method of claim 7, wherein the passive haptic actuator response is a rotation, a change in shape or a movement.

9. The method of claim 7, wherein the passive haptic actuator with the programmed polarity rotates at a rate of about 1-100 rotations/second to provide the passive haptic actuator response.

10. The method of claim 7, wherein the haptic device is implanted under skin of a hand of the user.

11. The method of claim 7, comprising providing and implanting multiple haptic devices under skin of a hand of the user.

12. The method of claim 11, wherein the passive haptic actuator response results from collective or sequential actuation of the haptic devices.

* * * * *